United States Patent [19]

Noel et al.

[11] Patent Number: 5,445,777
[45] Date of Patent: Aug. 29, 1995

[54] AIR LAYING FORMING STATION WITH BAFFLE MEMBER FOR PRODUCING NONWOVEN MATERIALS

[75] Inventors: John R. Noel, Cincinnati; Mark R. Richards, Middletown; Edward H. Krautter, Cincinnati, all of Ohio

[73] Assignee: The Procter & Gamble Company, Cincinnati, Ohio

[21] Appl. No.: 353,650

[22] Filed: Dec. 8, 1994

[51] Int. Cl.[6] .......................... B27N 3/04; B27N 3/02
[52] U.S. Cl. .................... 264/113; 264/510; 264/518; 425/81.1
[58] Field of Search ............... 264/510, 518, 113; 425/81.1, 83.1

[56] References Cited

U.S. PATENT DOCUMENTS

| | | | |
|---|---|---|---|
| 4,043,513 | 8/1977 | Hoberg et al. | 241/24 |
| 4,284,495 | 8/1981 | Newton | 209/3.1 |
| 4,543,274 | 9/1985 | Mulder | 427/197 |
| 4,640,810 | 2/1987 | Laursen et al. | 264/518 |
| 4,701,294 | 11/1987 | Radwanski et al. | 264/518 |
| 4,904,440 | 2/1990 | Angstadt | 264/517 |
| 4,908,175 | 3/1990 | Angstadt | 264/113 |
| 4,927,346 | 5/1990 | Kaiser et al. | 425/81.1 |
| 4,927,582 | 5/1990 | Bryson | 264/113 |
| 5,091,077 | 2/1992 | Williams | 209/12 |
| 5,102,585 | 4/1992 | Pieper et al. | 264/37 |
| 5,118,409 | 6/1992 | Zaltman | 209/466 |
| 5,156,902 | 11/1992 | Pieper et al. | 428/206 |
| 5,227,107 | 7/1993 | Dickenson et al. | 264/113 |
| 5,244,099 | 9/1993 | Zaltaman et al. | 209/466 |
| 5,350,597 | 9/1994 | Pelley | 427/197 |

FOREIGN PATENT DOCUMENTS 2150033 11/1983 United Kingdom .
2175024 4/1985 United Kingdom .

OTHER PUBLICATIONS

Vonderharr, et al. "Method and Apparatus for Forming an Intermittent Stream of Particles for Application to a Fibrous Web" Patent Application Oct. 19, 1993.

Richards, M. R., "Process For Adding AGM To An Air Laying Forming Station To Produce A Multi-Zone (Z Dimension) Substrate In Reference To AGM Concentration".

*Primary Examiner*—Mary Lynn Theisen
*Attorney, Agent, or Firm*—Michael D. Wiggins; Larry L. Huston

[57] ABSTRACT

An air laying forming station (ALFS) forms a nonwoven substrate from a first material and a second material having at least one physical characteristic substantially different from the first material. The ALFS includes a forming chamber and a forming screen, moving relative to the forming chamber, for receiving deposit of the first and second materials. A first distributor supplies the first material. A vacuum source provides an air flow which deposits the first material onto the forming screen. A second distributor delivers the second material, independently from the first material between the first distributor and the forming screen, by gravity along one or more baffle members.

20 Claims, 4 Drawing Sheets

AIR LAYING FORMING STATION WITH BAFFLE MEMBER FOR PRODUCING NONWOVEN MATERIALS

BACKGROUND OF THE INVENTION

1. Technical Field

This invention relates to air laying forming stations and, more particularly, to air laying forming stations for producing nonwoven materials from first and second materials having a difference in characteristic or composition and including a baffle member for directing the flow of the second material by gravity and independently of the first material.

2. Discussion

Conventional air laying forming stations (ALFS) use one air stream to transport and distribute blends of materials which are different in characteristic or composition, for example high absorbency materials (HAM) and fibrous materials (FM). As differences between the materials (such as size, shape, and density) increase, the materials behave differently in the common air stream and undesirable and uncontrollable separation of the blend occurs. Separation problems increase as the flow distance increases and as the width of the ALFS and the nonwoven material increase in the cross machine direction (CD). Such increasing distances, widths and behavioral differences of the materials in the air stream result in highly variable basis weights in the machine direction (MD) and the CD. Conventional ALFS have typically been unable to provide uniform and controlled distribution of HAM in nonwoven materials, especially as CD widths approach and exceed 1 meter. Additionally, conventional ALFS have been unable to uniformly and controllably distribute HAM in nonwoven materials as mass concentrations of HAM approach and exceed 15-20% by weight.

As a result of transporting the blend of materials in a single air stream, the conventional ALFS generally produce only nearly homogenous blends of HAM and FM and cannot produce nonwoven materials having multiple zones of HAM and FM concentrations in the Z-axis (orthogonal to the MD and CD). Thus, a single conventional ALFS cannot produce a nonwoven material with nearly HAM-free or reduced-HAM dusting zones in order to better contain the HAM within the nonwoven material during further processing and consumer use. Benefits of providing multiple HAM concentration zones along the Z-axis are well recognized within the art for various applications, including diapers, feminine hygiene products, etc. The art generally focuses on two key benefits of variable HAM concentration zones. The first is an improvement to HAM efficiency and effectiveness, and the second is improved containment of HAM within the structure.

Transporting the HAM and FM to form absorbent bodies using separate air streams has been proposed, for example in U.S. Pat. No. 4,927,582 to Bryson. In Bryson, blower 48 propels HAM 28 via one or more pipeline conduits 20 into forming chamber 10. Vacuum source 32 creates an air flow, indicated by arrows 36, which draws FM 14 against forming screen 30. Baffles 34 are attached to opposing sidewalls (e.g. in a CD) and are used to regulate the cross-directional distribution of HAM across web 41.

In use, however, air injection to propel HAM 28 into forming chamber 10 disrupts the flow of FM 14 onto forming screen 30 adversely affecting uniform distribution of FM 14. Use of one or more pipeline conduits 20 provides poor CD control of the basis weight of HAM 28 deposited onto forming screen 30, particularly for wide machines (in the CD). In addition, the use and positioning of baffles 34 disrupts FM 14 formation on forming screen 30.

In Bryson, HAM and FM are introduced separately, however CD basis weight profiling of HAM 28 is accomplished after HAM 28 mixes with FM 14 using baffles 34. Profiling HAM 28 using baffles 34 as disclosed in Bryson also changes the CD basis weight profile of FM 14. Thus, independent CD basis weight profiling of FM 14 and HAM 28 is not achieved.

Therefore, an ALFS which forms a nonwoven material with reduced MD and CD variability of a second material, (for example HAM) within a first material (for example FM) which has a significant difference in characteristic or composition is desirable. Additionally, an ALFS which forms a nonwoven material by providing control of the Z-axis placement of a second material (for example HAM) within a first material (for example FM) which has a significant difference in characteristic or composition is desirable.

SUMMARY OF THE INVENTION

An air laying forming station (ALFS) according to the invention, forms a nonwoven material from a first material and a second material having at least one characteristic different from said first material. The ALFS includes a forming chamber and a forming screen moving relative to said forming chamber, for receiving deposit of said first and second materials. A first material distributor or distributors distributes said first material. A flow device provides an air flow which deposits said first material onto said forming screen. A second material distributor distributes said second material, independently from said first material, by gravity, between said first material distributor and said forming screen.

According to one feature of the invention, the second material distributor employs a baffle member along which said second material is transported in order to direct the flow of said second material by gravity.

According to another feature of the invention, the baffle member of said second material distributor introduces said second material into the forming chamber of the ALFS.

According to still another feature of the invention, the baffle member includes upper and lower planar sections defining an angle therebetween.

According to still another feature of the invention, the baffle member includes an arcuate section or sections.

According to yet another feature of the invention, a cover is provided for said baffle member to reduce the disruption of said second material as it is being distributed and directed by said baffle member.

Still other features will be readily apparent.

BRIEF DESCRIPTION OF THE DRAWINGS

The various advantages of the present invention will become apparent to skilled artisans after studying the following specification and by reference to the drawings in which:

FIG. 2 is a cross-sectional view of a nonwoven material taken along line 2—2 in FIG. 1;

DESCRIPTION OF THE PREFERRED EMBODIMENT

While the background discussion was primarily limited to discussions of problems with air laying forming stations (ALFS) for producing absorbent bodies, including high absorbency materials (HAM) and fibrous materials (FM), skilled artisans will appreciate that the foregoing description applies to nonwoven materials incorporating other materials.

Figure 1:
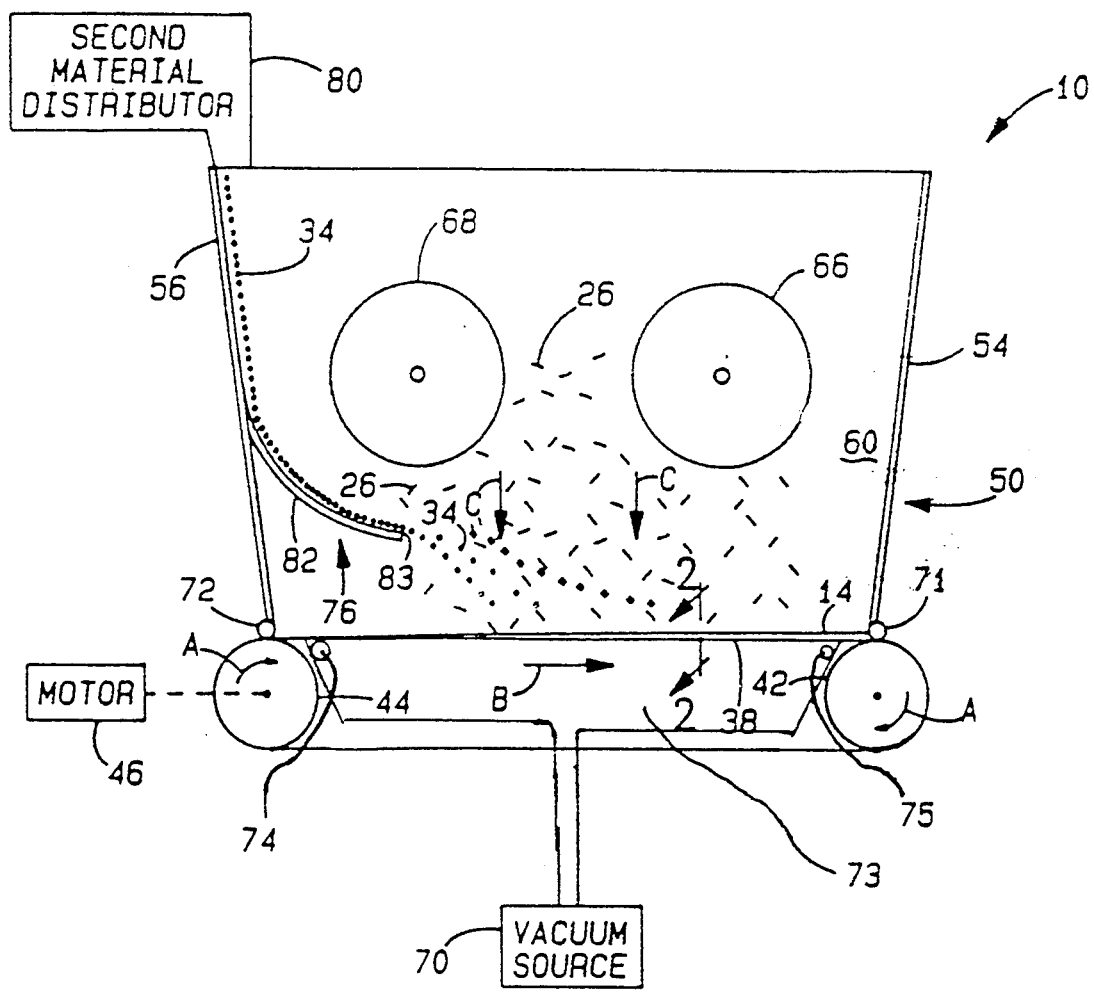
FIG. 1 is a side view of an air laying forming station according to a first embodiment of the present invention.

FIG. 1 illustrates a side cross-sectional view of ALFS 10. Skilled artisans can appreciate that ALFS 10 can accommodate variable widths in the CD. The length and height of ALFS 10 in the MD and Z-axis directions, respectively, can also be varied as desired. In FIG. 2, the Y-axis indicates the MD, the X-axis indicates the cross-machine direction (CD), and the Z-axis indicates the thickness of the nonwoven material. The Z-axis is orthogonal to the X and Y-axis. ALFS 10 according to the invention produces nonwoven material 14 with Z-axis zones of controlled concentrations of first material 26 and a second material 34. For example, ALFS 10 according to the invention produces nonwoven material 14 which includes dusting zones 18 and 22, each containing predominantly and preferably only first material 26 surrounding a middle zone 30 which is a nearly homogenous mix of first material 26 and second material 34. Outer dusting zones 18 and 22 provide surfaces with significantly reduced concentrations (preferably free) of second material 34, that act as barriers, to reduce the loss of second material 34 during further processing and consumer use. Outer dusting layers 18 and 22 are described in further detail in commonly assigned U.S. Pat. No. 4,904,440, entitled "Apparatus for and Methods of Airlaying Fibrous Webs Having Discrete Particles Therein" and U.S. Pat. No. 4,908,175, entitled "Apparatus for and Methods of Forming Airlaid Fibrous Webs having a Multiplicity of Components" each hereby incorporated by reference.

First material 26 has at least one characteristic different than second material 34. For example, first material 26 can have a blend ratio, composition, size, shape, density, hydrophilicity, absorbency, chemistry, function, etc. which is different than one or more corresponding characteristics of second material 34. First material 26 and second material 34 can be blends of or pure cellulose or wood pulp fibers which can be natural, or chemically, mechanically, or thermally modified, stiffened, or cross-linked; synthetic fibers such as staple or matrix fibers (polyester for example) or bonding fibers (polyethylene/polypropylene bicomponent for example); super absorbent fibers, particles, powders, or foams; odor control particles or powders; adhesive or bonding particles or powders; etc. Still other types of materials will be apparent to skilled artisans.

ALFS 10 of FIG. 1 produces nonwoven material 14 on a forming screen 38 which preferably moves relative to ALFS 10. For example, forming screen 38 can be in the form of an endless belt mounted on support rollers 42 and 44. A suitable driving means, for example an electric motor 46, rotates at least one of the support rollers 42 or 44 in a direction indicated by arrows "A" at a selected speed. As a result, forming screen 38 moves in a machine direction (MD) indicated by arrow "B".

Forming screen 38 can be provided in other forms, for example in the form of a circular drum which can be rotated using a motor as disclosed in Bryson U.S. Pat. No. 4,927,582. Alternately, ALFS 10 can move relative to stationary forming screen 38, or both ALFS 10 and forming screen 38 can move relative to each other. Preferably forming screen 38 is made of plastic, however, metal such as bronze is also an acceptable material for forming screen 38. Forming screen 38 can be an Electrotech 4 distributed by Albany International located in Portland, Tenn. As can be appreciated by skilled artisans, other forming screens 38 can be employed.

ALFS 10 further includes a forming chamber 50 with downstream and upstream endwalls 54 and 56, respectively. Sidewalls 60, connecting opposing ends of downstream and upstream endwalls 54 and 56, respectively, are also provided. ALFS 10 employs first material distributors 66 and 68 which provide the desired distribution of first material 26 inside forming chamber 50 across the desired width in the CD. Preferably, first material distributors 66 and 68 are rotating cylindrical distributing screens. Such distributing screens are disclosed in detail in U.S. Pat. No. 4,640,810 entitled "System for Producing an Air Laid Web", hereby incorporated by reference. First material 26 is fed into the interior of first material distributing screens 66 and 68. As first material distributing screens 66 and 68 rotate, first material 26 is delivered uniformly through the rotating cylindrical screens. While first material distributing screens 66 and 68 are disclosed, one or more other suitable distributors are contemplated and can be employed.

ALFS 10 may also include a vacuum source 70, such as a conventional blower, for creating a selected pressure differential through forming chamber 50 to draw first material 26 out of distributors 66 and 68 against forming screen 38. Seal rollers 71 and 72 reduce vacuum loss between forming chamber 50 and forming screen 38. Preferably, vacuum source 70 is a blower connected to vacuum box 72 which is located underneath forming chamber 50 and forming screen 38. Vacuum source 70 creates an airflow, indicated by arrows "C" in FIG. 1, through forming chamber 50 and forming screen 38 into vacuum box 72. Vacuum box 72 can include seal deckles 74 and 75 which directly contact forming screen 38 approximately below seal rollers 71 and 72. Air flow "C" causes and directs the deposit of first material 26 and, to a lesser extent, the deposit of second material 34 on forming screen 38.

A baffle member 76 directs second material 34 supplied by a second material distributor 80 into forming chamber 50, underneath first material distributors 66 and 68 and onto forming screen 38. Preferably, second material distributor 80 distributes second material 34 across a desired width, in a desired pattern, in the CD, and second material 34 is conveyed primarily by gravity.

Figure 3A:
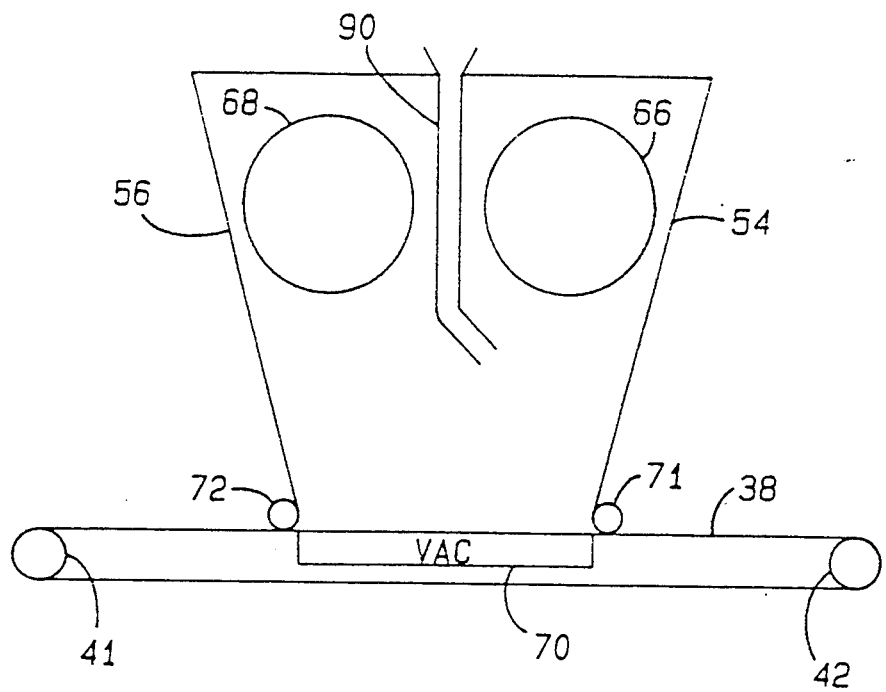
FIG. 3A is a side view of an air laying forming station according to a second embodiment of the present invention.
Figure 3B:
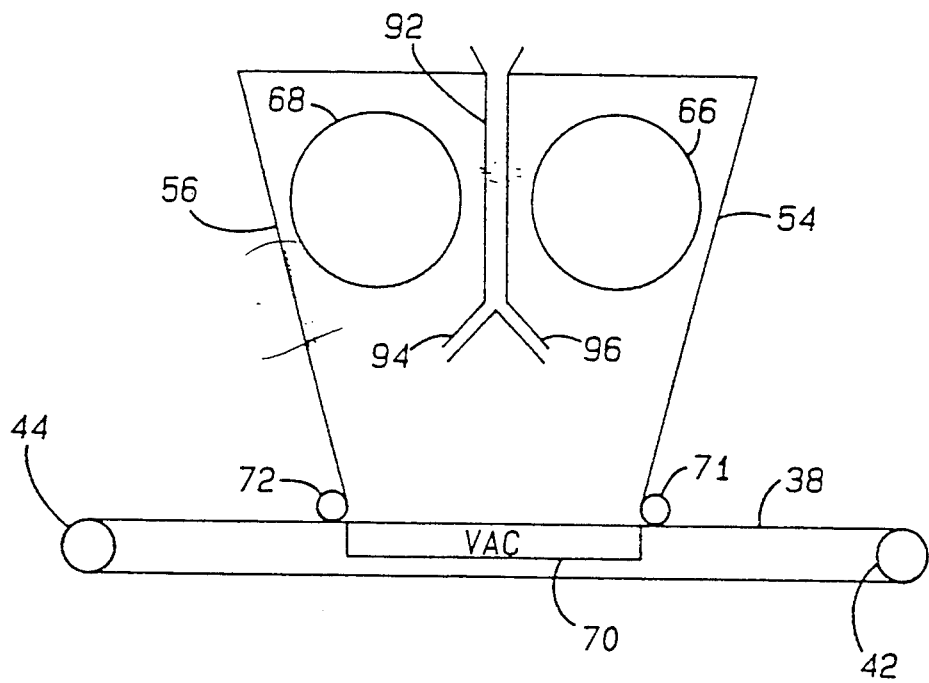
FIG. 3B is a side view of an air laying forming station similar to FIG. 3A but with a dual exit baffle member according to a third embodiment of the present invention.

Baffle member 76 can be adjacent to upstream endwall 56, as shown in FIG. 1. Alternately, baffle member 76 can be adjacent to downstream endwall 54 or both upstream and downstream endwalls 56 and 54, respectively. The baffle member 76 may extend from a midsection of the endwalls 56 and 54, as shown. Alternately, as illustrated in FIGS. 3A and 3B, a baffle member 90 can be located between first material distributors 66 and 68. Additionally, as illustrated in FIG. 3B, a baffle member 92 may have multiple exits 94 and 96. Baffle member 76, 90 and 92 can be an arcuate section as illustrated in FIG. 1. Alternately, baffle member 76 can consist of a single flat section, or preferably at least two flat sections connected at angles relative to each other, as will be described in conjunction with FIG. 4. Other shapes will be readily apparent to skilled artisans. Preferably, baffle member 76 has a width approximately equal to first material distributors 66 and 68 and the desired nonwoven material width in the CD.

In use, motor 46 rotates support rollers 42 and 44 which moves forming screen 38 relative to forming chamber 50. Vacuum source 70 creates air flow "C" which draws first material 26 supplied by first material distributors 66 and 68 onto forming screen 38. Second material distributor 80 meters and distributes flow of second material 34, independent of first material 26. Second material 34 falls primarily by gravity along baffle member 76 onto forming screen 38. As such, ALFS 10 according to the invention delivers distributed second material 34 by gravity between first material distributors 66 and 68 and forming screen 38 and separate and independent of delivery of first material 26. ALFS 10 provides uniform delivery of first material 26 and second material 34 in the MD and CD. In other words, ALFS 10 according to the invention independently profiles both first material 26 and second material 34 before mixing the two materials in forming chamber 50. As such, undesirable and uncontrollable separation of the dissimilar materials within a common air stream is avoided, and ALFS 10 according to the invention significantly reduces the undesirable variability of second material 34 in X- and Y-axis directions (e.g. CD and MD) without significantly altering the deposition of first material 26 on forming screen 38. Baffle members 76, 90 and 92 are positioned to minimize the disruption of first material 26 formation. Importantly, ALFS 10 can be constructed to various widths in the X-axis direction or CD, and the variability of second material 34 in the MD and CD is not a function of ALFS 10 width in the X-axis direction or CD.

Typically, the flow of second material 34 from second material distributor 80 is constant and uniform in both the MD (i.e. time) and the CD, however, if nonwoven material needs dictate, the flow of second material 34 can be patterned in the MD and CD by appropriate design modifications to second material distributor 80. For example, the baffle member 76 may have grooves or channels, to provide a striped effect to the second material 34. This yields a second material 34 distribution which is cyclic, and repeating in the CD. Such a cyclic repeating pattern of second material 34 is considered to be substantially uniform in the CD, due to the repeating nature, just as a second material 34 distributed without a repeating pattern is considered substantially uniform hereunder. The basis is that at any CD location, in either configuration, the second material 34 distribution substantially matches that at other CD locations. In conjunction with the use of the subject baffles, patterned flow of second material 34 allows for the production of nonwoven materials with various and controlled concentration patterns of second material 34 in the MD, CD, and thickness of the nonwoven material. Various devices are known in the art which could be used as second material distributor 80, a preferred device for dispensing HAM is a dispensing machine for dusting, seeding, and topping of dry materials. Specifically, model Coat-O-Matic 23.62-DE-S sold by Christy Machine Company in Fremont, Ohio.

Figure 4:
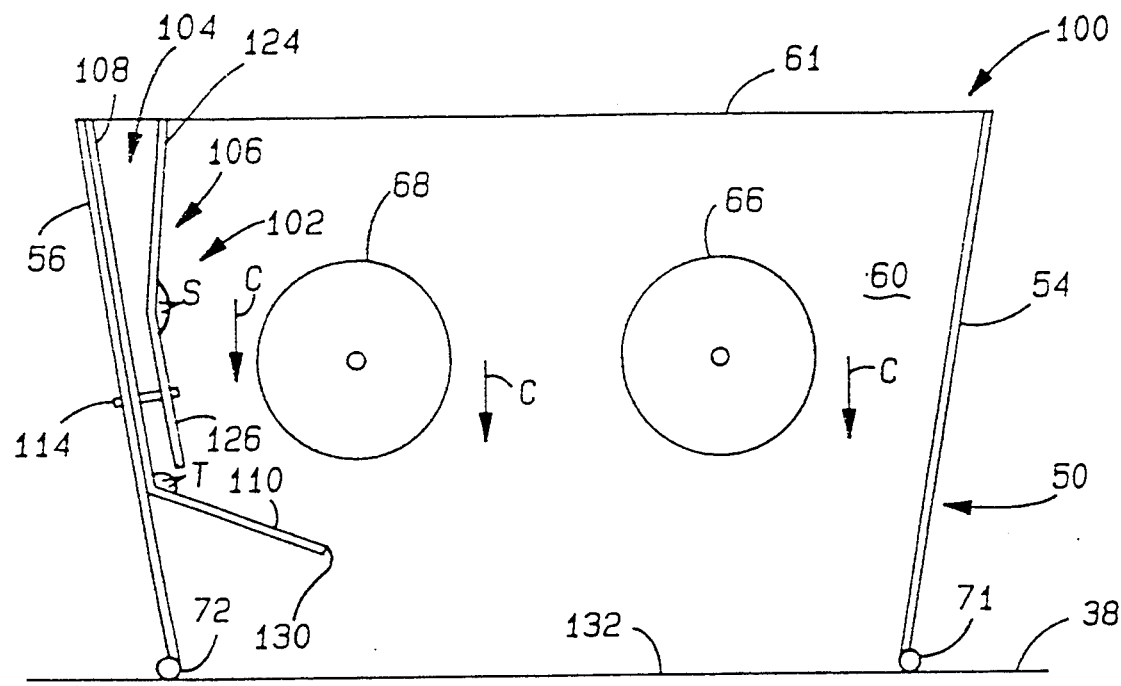
FIG. 4 is a side view of an air laying forming station according to a fourth embodiment of the present invention.

In FIG. 4, a presently preferred embodiment, ALFS 100, is illustrated. For purposes of clarity, reference numbers from FIGS. 1 and 2 will be used in FIG. 4 where appropriate. In addition, details, for example motor 46, vacuum source 70, etc., have been omitted to simplify FIG. 4.

ALFS 100 includes a fixture 102 with a baffle member 104 and a cover 106. Baffle member 104 preferably includes upper and lower planar sections 108 and 110, respectively. Upper planar section 108 is attached to upstream endwall 56 in any suitable manner, for example glue, solder, bolts, clamps, etc. Other suitable means of attaching upper planar section 108 of baffle member 104 to endwall 56 will be apparent to skilled artisans. Lower planar section 110 forms an angle "T" with respect to upper planar section 108. Preferably, upper and lower planar sections 108 and 110, respectively, are formed from a single planar section of material which has been bent. LEXAN ® is a preferred material of construction for fixture 102. Preferably the LEXAN ® has a thickness of 0.25 inches.

The cover 106 is mounted adjacent to upper planar section 108 of baffle member 104 using any suitable means which does not significantly interrupt the flow of second material 34 passing along upper and lower planar sections 108 and 110, respectively. The cover 106 may also be made of LEXAN ® and has a thickness of about 0.25 inches. For example, spacers 114 corresponding to the desired clearance between cover 106 and upper planar section 108 of baffle member 104 can be glued to the inner surfaces of cover 106 and upper planar section 108 of baffle member 104. Other suitable means of attaching cover 106 to upper planar section 108 of baffle member 104 will be apparent to skilled artisans. Clearance between baffle member 104 and cover 106 should be as small as possible, but sufficient to allow a desired maximum flow of second material 34 to pass there between. A typical clearance is 0.1875 inch. Upper planar section 124 of cover 106 and upper planar section 108 of baffle member 104 can be adapted to support second material distributor 80. Lower planar section 126 and upper planar section 124 of cover 106 form an angle "S" with respect to each other. Angle "S" should be as great as possible, but sufficiently small to allow the space between upper planar section 108 of baffle member 104 and upper planar section 124 of cover 106 to be great enough to capture the entire output of second material distributor 80. A typical value for angle "S" is 140 degrees although higher and lower angles can be employed.

The lower planar section 126 of cover 106 extends toward angle "T" and preferably ends at a distance from lower planar section 110 of baffle member 104 such that the clearance between the end of lower planar section 126 of cover 106 and lower planar section 110 of baffle member 104 is equal to the clearance between baffle member 104 and cover 106. However, lower planar section 126 of cover 106 may extend further such that it lies parallel to lower planar section 110 of baffle member 104 beyond angle "T". A sufficient clearance must also be maintained in this case. Thus, lower planar section 126 of cover 106 would also have to contain an angle equivalent to angle "T".

Figure 5:
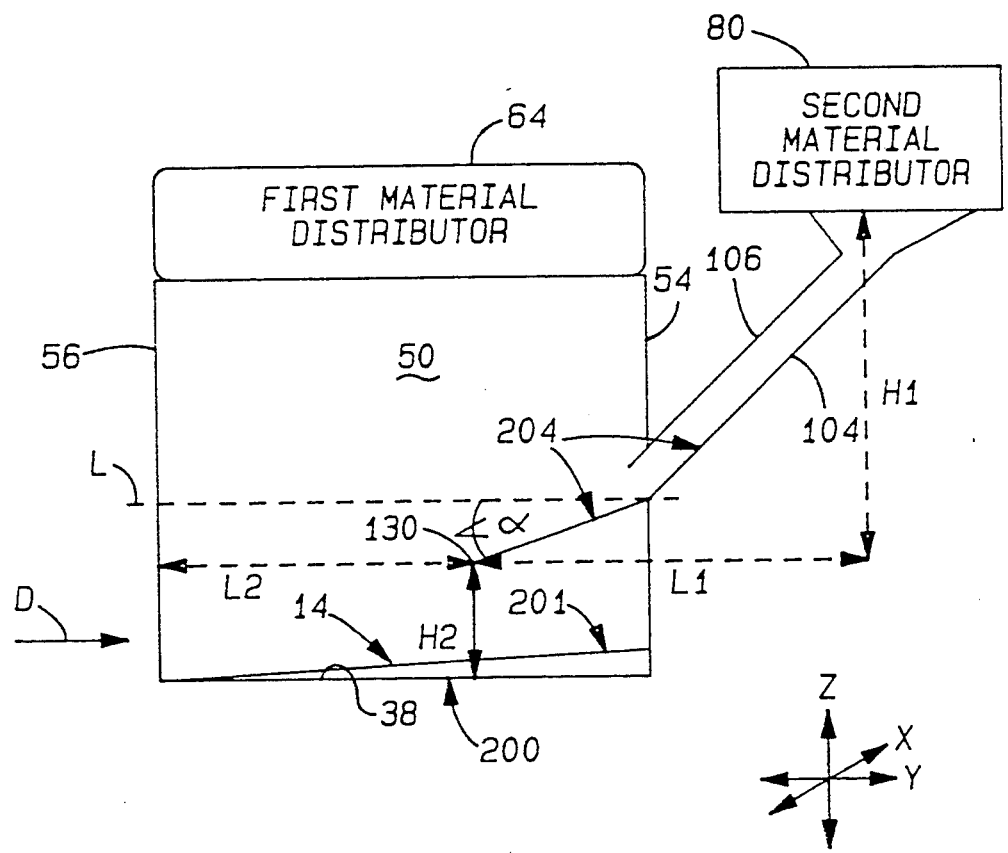
FIG. 5 is a side view of an air laying forming station according to the invention illustrating parameters affecting the distribution of materials 1 and 2 within the nonwoven material.

In FIG. 5, important design parameters for baffle member 104 of ALFS 100 are illustrated in further detail. For purposes of clarity, reference numbers from FIGS. 1, 2, and 4 will be used in FIG. 5 where appropriate. In addition, details, for example motor 46, vacuum source 70, etc., have been omitted to simplify FIG. 5. Alternately, baffle member 104 including cover 106 can be independent of endwalls 56 and/or 54 and can introduce second material 34 from either or both endwalls 56 or 54. These design parameters affect the Z-axis position of second material 34 within nonwoven material 14. More specifically, these design parameters affect the Z-axis location of second material 34 within nonwoven material 14 by the specific location of the tip of baffle member 104 and by controlling the momentum vector of second material 34 as it leaves baffle tip 130 of baffle member 104. It should be noted that the basic design principles are discussed in specific reference to the ALFS design illustrated in FIG. 5. These principles can be easily translated to other ALFS designs discussed in this disclosure.

The basis weight and thickness of nonwoven material 14 gradually increase as nonwoven material moves in the machine direction, as indicated by arrow "D", through forming zone 50. This is illustrated by the thickness difference of nonwoven material 14 near upstream endwall 56 as compared to near downstream endwall 54. The initial elements of first material 26 which fall onto forming wire 38 near upstream endwall 56 form wire-side surface 200 within nonwoven material 14. As forming wire 38 continues to move in the machine direction through forming zone 50, additional elements of first material 26 fall onto the building surface of nonwoven material 14 continually increasing the basis weight and thickness of nonwoven material 14 until the final elements of first material 26 fall onto the surface of nonwoven material 14 near downstream endwall 54 forming non-wire-side surface 201 within nonwoven material 14. The Z-axis location of any element of first material 26 depends on where that element falls onto the building surface of nonwoven material 14 along the machine direction axis within forming zone 50 relative to endwalls 54 and 56. Elements of first material 26 that fall onto the building surface of nonwoven material 14 in forming chamber 50, near upstream endwall 56 will have a Z-axis location near wire-side surface 200 within nonwoven material 14. Elements of first material 26 that fall onto the building surface of nonwoven material 14 in forming chamber 50, near downstream endwall 54 will have a Z-axis position near non-wire-side surface 201 within nonwoven material 14. Elements of first material 26 that fall onto the building surface of nonwoven material 14 more intermediate between endwalls 54 and 56 will have a Z-axis position more intermediate between surfaces 200 and 201 within nonwoven material 14.

The Z-axis location of second material 34 within nonwoven material 14 follows a similar pattern. If second material 34 falls onto the building surface of nonwoven material 14 near upstream endwall 56, second material 34 will have a Z-axis location near wire-side surface 200 within nonwoven material 14. If second material 34 falls onto the building surface of nonwoven material 14 near downstream endwall 54, second material 34 will have a Z-axis location near non-wire-side surface 201 within nonwoven material 14. If second material 34 falls onto the building surface of nonwoven material 14 more intermediate between endwalls 54 and 56, second material 34 will have a Z-axis location more intermediate between surfaces 200 and 201 within nonwoven material 14.

The momentum vector of second material 34 as it leaves baffle tip 130 of baffle member 104 along with the specific location of baffle tip 130 of baffle member 104 determine, to a large extent, where, along the machine direction (Y-axis), second material 34 falls onto the building surface of nonwoven material 14 within forming chamber 50 and thus the Z-axis location of second material 34 within nonwoven material 14.

The momentum vector includes both a magnitude and a direction. Both are important in determining the Z-axis location of second material 34 within nonwoven material 14. Both can be affected by the design parameters of baffle member 104.

The magnitude of the momentum vector is a function of mass and velocity, but since mass is fixed for a given second material 34, the magnitude of the momentum vector is basically a function of the velocity of second material 34 when it leaves baffle tip 130 of baffle member 104. Second material 34 with a relatively large momentum vector magnitude will fall closer to upstream endwall 56 and therefore have a Z-axis location relatively closer to wire-side surface 200 within nonwoven material 14. Conversely, second material 34 with a relatively small momentum vector magnitude will fall closer to downstream endwall 54 and therefore have a Z-axis location relatively closer to non-wire-side surface 201 within nonwoven material 14. Further, an ALFS according to the invention utilizes gravity to impart velocity to second material 34. Design parameters of baffle member 104 control the effect of gravity on second material 34 control the velocity of second material 34 in other words, the design parameters effect the magnitude of the momentum vector of second material 34 and therefore the Z-axis location of second material 34 within nonwoven material 14. Examples of design parameters which provide this control are the vertical height H1 of second material distributor 80 above baffle tip 130 of baffle member 104, the horizontal distance L1 between the second material distributor 80 and baffle tip 130 of baffle member 104, and the roughness of upper surface 204 of baffle member 104. Relatively high values of second material distributor height H1, relatively low values of horizontal distance L1 and relatively smooth surfaces 204 tend to produce the highest velocities of second material 34 as it leaves baffle member 104. Conversely, relatively low vertical distances H1, relatively high horizontal distances L1 and relatively rough surfaces 204 tend to produce the lowest velocities of second material 34 as it leaves baffle member 104. Other design parameters for controlling the magnitude of the momentum vector will be obvious to skilled artisans.

Second material 34 is most often a blend of elements of various sizes and masses. Since gravity acts on each individual element rather than on second material 34 as a whole, the momentum vector's magnitude varies from element to element. The relatively high mass elements have a momentum vector with a relatively high magnitude and tend to travel further from baffle tip 130 of baffle member 104 within forming chamber 50 before being deposited on the building surface of nonwoven material 14. The relatively high mass elements therefore have a Z-axis location closer to wire-side surface 200 within nonwoven material 14. The converse should be expected for the relatively low mass elements.

With continued specific reference to the ALFS illustrated in FIG. 5, the distribution of the various individual elements composing second material 34 will tend to be stratified with the higher mass elements located closer to wire-side surface 200 within nonwoven material 14 and the lower mass elements located closer to non-wire-side surface 201 within nonwoven material 14. This Z-axis stratification by element mass can be advantageous in many product applications, especially those where nonwoven material 14 is an absorbent core for a disposable absorbent article and second material 34 is a particulate superabsorbent material.

The direction segment of the momentum vector indicated by an angle "$\alpha$" in FIG. 5, describes the direction in which second material 34 is traveling when it leaves baffle tip 130 of baffle member 104. Angle "$\alpha$" is formed by lower planar section 110 of baffle member 104 and a line "L" which is parallel to forming screen 38. When "$\alpha$" is small, second material 34 is traveling predominantly in a horizontal direction when it leaves baffle tip 130 of baffle member 104. When "$\alpha$" is large in value (upward or downward), second material 34 is traveling predominantly in a vertical direction when it leaves baffle tip 130 of baffle member 104. Relatively low values of "$\alpha$" will tend to deposit second material 34 on the building surface of nonwoven material 14 relatively close to upstream endwall 56 within forming chamber 50 and therefore second material 34 will have a Z-axis location relatively close to wire-side surface 200 within nonwoven material 14. Conversely, relatively high values of "$\alpha$" will tend to deposit second material 34 on the building surface of nonwoven material 14 relatively close to downstream endwall 54 within forming chamber 50 and therefore second material 34 will have a Z-axis location relatively close to non-wire-side surface 201 within nonwoven material 14.

The specific location of baffle tip 130 of baffle member 104 is also critical to the Z-axis location of second material 34 within nonwoven material 14. The critical aspects of location are vertical height H2 of baffle tip 130 above forming wire 38 and horizontal distance L2 between baffle tip 130 and upstream endwall 56. Larger values of vertical height H2 allow second material 34 to travel further in the horizontal plane and thus be deposited on the building surface of nonwoven material 14 closer to upstream endwall 56 and, therefore, second material 34 will have a Z-axis location closer to wire-side surface 200 within nonwoven material 14. Larger values of horizontal distance L2 cause second material 34 to be deposited on the building surface of nonwoven material 14 further from upstream endwall 56 and, therefore, second material 34 will have a Z-axis location closer to non-wire-side surface 201 within nonwoven material 14.

The following are examples of nonwoven material compositions which can be produced using ALFS 100:

First material 26 is a blend of 85% cellulose wood pulp (Weyerhaeuser NB416, for example) and 15% polyethylene/polypropylene bicomponent bonding fiber (Danaklon ES-C 1.7 dtex×6 mm, for example). Second material 34 is a super absorbent particle (Nalco 1180, for example). The mass ratio of first material 26 to second material 34 is approximately 1:1.

First material 26 is a blend of 70% cellulose wood pulp (Weyerhaeuser NB416, for example) and 20% polyethylene/polypropylene bicomponent bonding fiber (Danaklon ES-C 1.7 dtex×6 mm, for example) and 10% super absorbent particle (Nalco 1180, for example). Second material 34 is a super absorbent particle (Nalco 1180 for example). The mass ratio of first material 26 to second material 34 is approximately 2:1.

First material 26 is a blend of 50% NB416 and 50% polyester staple/matrix fiber (Hoechst Celanese T183 15 dpf×0.5 inch, for example). Second material 34 is an odor control agent (Activated Charcoal, PCB by Calgon, for example). The mass ratio of first material 26 to second material 34 is approximately 5:1.

First material 26 is a blend of 85% cellulose wood pulp (Weyerhaeuser NB416, for example) and 15% polyethylene/polypropylene bicomponent bonding fiber (Danaklon ES-C 1.7 dtex×6 mm, for example). Second material 34 is a polyethylene powder bond agent (Veraplast Vertene Neutro 200, for example). The mass ratio of first material 26 to second material 34 is approximately 6:1.

First material 26 is a blend of 75% cellulose wood pulp (Weyerhaeuser NB416, for example) and 25% super absorbent fiber (Fibersorb Type 1700 produced by Arco Chemical for example). Second material 34 is a blend of 75% grass seed and 25% dry fertilizer. The mass ratio of first material 26 to second material 34 is approximately 1:2. Other nonwoven material compositions will be readily apparent to skilled artisans.

Figure 6:
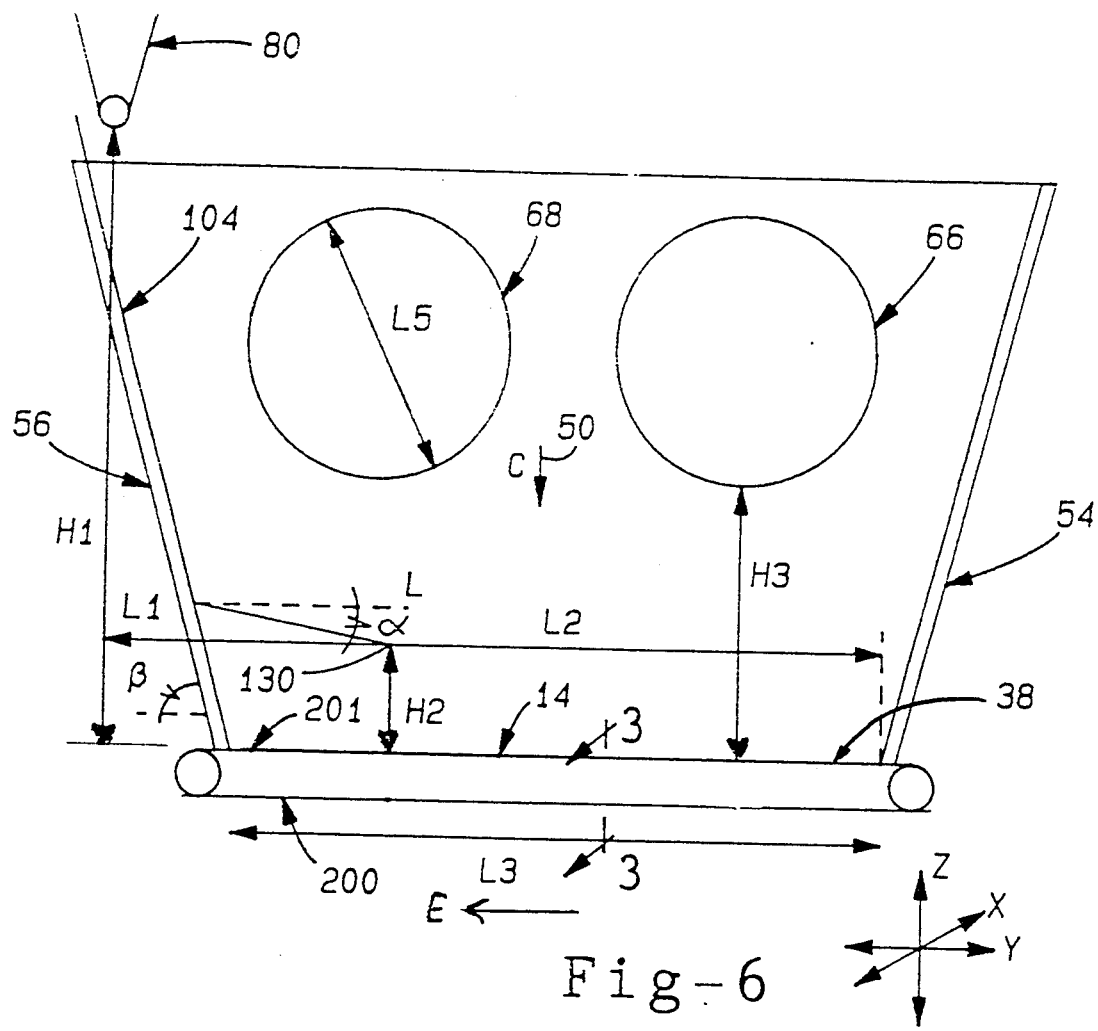
FIG. 6 is a simplified side view of an air laying forming station according to the invention illustrating example baffle member set-up parameters and the resultant nonwoven material structures.
Figure 7:
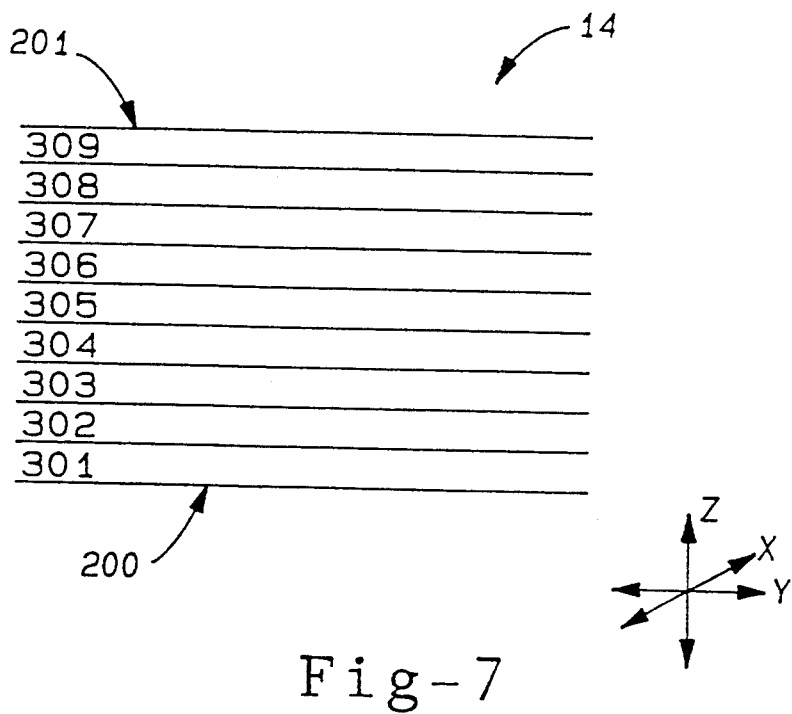
FIG. 7 is a cross-sectional view of an illustrative nonwoven material taken along section 3—3 of FIG. 6.

FIG. 6 illustrates example set-up parameters and FIG. 7 illustrates the resultant nonwoven material 14 structures created thereby. The ALFS of FIG. 6 (excluding elements of the invention) is a Dan Web Lab Former as supplied by Dan-Webforming Int. LTD. of Aarhus, Denmark, and which has a machine direction E. First material distributor 80 is a model Coat-O-Matic 23.62-DE-S dispensing machine sold by Christy Machine Company of Fremont, Ohio. In these examples, first material 26 is blend of 67% (by mass) Flint River Southern Softwood Kraft pulp and 33% (by mass) Danaklon ES-C 1.7 dtex×6 mm Bicomponent Bonding Fiber, second material 34 is Nalco 1180 High Absorbency Material. First material 26 and second material 34 were distributed by first material distributors 66 and 68 and second material distributor 80, respectively, at rates such that the resultant nonwoven material 14 consists of 71.7% (by mass) first material 26 and 28.3% (by mass) second material 34. The Flint River Southern Softwood Kraft pulp was prepared by defibrating dry lap of the same material with a Dan Web Defibrator Model Number 140. Since individual nonwoven material 14 structures have unique benefits relative to a given final application need, a single preferred set of set-up parameters cannot be identified. As such, Tables 1-3 gives examples of set-up parameters relative to FIG. 6 and a description of the resultant nonwoven material 14.

For purposes of clarity, reference numbers from FIGS. 1, 2, 4, and 5 will be used in FIG. 6 where appropriate. In addition, details, for example motor 46, vacuum source 70, etc., have been omitted to simplify FIG. 6. As can be appreciated from FIG. 6, cover member 106 can be omitted. Parameters associated with the specific ALFS under consideration which aid in the illustration of the examples are given. Angle "$\beta$" is the angle made by endwall 56 with respect to forming screen 38. As indicated in FIG. 6, "$\beta$" is equal to 78 degrees and is held constant for all examples given. Vertical distance H3 is the distance between the bottom surfaces of first material distributors 66 and 68. As indicated in FIG. 6, H3 is equal to 13.5 inches and is held constant for all examples given. Horizontal distance L3 is the distance between seal rolls 71 and 72 along forming screen 38. As indicated in FIG. 6, L3 is equal to 20 inches and is held constant for all examples given. Horizontal distance L5 is the diameter of first material distributors 66 and 68. As indicated in FIG. 6, L4 is equal to 11.75 inches and is held constant for all examples given.

FIG. 7 illustrates the example nonwoven material 14 structures given as illustrative examples in Tables 1–3. The Z-axis or thickness dimension of nonwoven material 14 is divided into 9 zones which are numbered 301 through 309, consecutively, with one surface of zone 301 being wire-side surface 200 of nonwoven material 14 and one surface of zone 309 being non-wire-side surface 201 of nonwoven material 14.

In Tables 1–3, with reference to FIGS. 6–7, examples are offered to illustrate the effect of some baffle member 104 set-up parameters on the Z-axis distribution of materials 1 and 2 in nonwven material 14.

TABLE 1

$\alpha = 18°$ H1 = 37.25 inches H2 = 9 inches L1 = 5.5 inches
L2 = 16.6 inches
Material of Construction is Smooth Lexan

| Zone | First Material Basis Weight | Second Material Basis Weight | % Second Material by Mass |
|---|---|---|---|
| 309 | 22.2 gsm | 2.6 gsm | 10.5% |
| 308 | 22.9 gsm | 2.4 gsm | 9.5% |
| 307 | 24.3 gsm | 3.0 gsm | 11.0% |
| 306 | 30.7 gsm | 6.9 gsm | 18.4% |
| 305 | 31.5 gsm | 9.9 gsm | 23.9% |
| 304 | 29.1 gsm | 18.2 gsm | 34.5% |
| 303 | 26.9 gsm | 22.3 gsm | 45.3% |
| 302 | 24.5 gsm | 16.6 gsm | 40.4% |
| 301 | 26.2 gsm | 11.9 gsm | 31.2% |
| Total | 238.3 gsm | 93.8 gsm | 28.3% |

TABLE 2

$\alpha = 48°$ H1 = 37.25 inches H2 = 6.75 inches L1 = 2.75 inches
L2 = 19.75 inches
Material of Construction is Smooth Lexan

| Zone | First Material Basis Weight | Second Material Basis Weight | % Second Material by Mass |
|---|---|---|---|
| 309 | 26.0 gsm | 13.3 gsm | 33.9% |
| 308 | 30.5 gsm | 26.3 gsm | 46.3% |
| 307 | 31.4 gsm | 28.2 gsm | 47.3% |
| 306 | 34.5 gsm | 20.6 gsm | 37.4% |
| 305 | 36.5 gsm | 9.2 gsm | 20.0% |
| 304 | 34.0 gsm | 6.1 gsm | 15.2% |
| 303 | 30.5 gsm | 5.0 gsm | 14.0% |
| 302 | 28.3 gsm | 1.9 gsm | 6.3% |
| 301 | 31.7 gsm | 1.3 gsm | 3.9% |
| Total | 283.4 gsm | 111.8 gsm | 28.3% |

TABLE 3

$\alpha = 48°$ H1 = 37.25 inches H2 = 9.3 inches L1 = 4.5 inches
L2 = 17.75 inches
Material of Construction is Smooth Lexan

| Zone | First Material Basis Weight | Second Material Basis Weight | % Second Material by Mass |
|---|---|---|---|
| 309 | 23.9 gsm | 1.2 gsm | 4.7% |
| 308 | 31.3 gsm | 3.0 gsm | 8.8% |
| 307 | 34.1 gsm | 15.6 gsm | 31.3% |
| 306 | 33.9 gsm | 27.0 gsm | 44.4% |
| 305 | 35.4 gsm | 29.0 gsm | 45.0% |
| 304 | 34.7 gsm | 20.8 gsm | 37.4% |
| 303 | 31.9 gsm | 10.9 gsm | 25.5% |
| 302 | 29.4 gsm | 4.7 gsm | 13.7% |
| 301 | 32.5 gsm | 1.2 gsm | 3.6% |
| Total | 287.2 gsm | 113.4 gsm | 28.3% |

The various advantages of the present invention will become apparent to those skilled in the art after a study of the foregoing specification and following claims.

What is claimed is:

1. An air laying forming station (ALFS) for forming a nonwoven substrate from a first material and a second material having at least one physical characteristic substantially different from said first material, comprising:
   a forming chamber;
   forming means, moving relative to said forming chamber, for receiving deposit of said first and second materials;
   first distributing means for supplying said first material; flow means for providing an air flow which deposits said first material onto said forming means; and
   second distributing means for delivering said second material, independently from said first material between said first distributing means and said forming means, by gravity along a baffle member.

2. The ALFS of claim 1 wherein said upstream and downstream endwalls are inclined with respect to said forming means, wherein said baffle member is connected to at least one of said upstream and downstream endwalls, and wherein said second distributing means delivers said second material along said at least one of said upstream and downstream endwalls and on said baffle member.

3. The ALFS of claim 2 wherein said baffle member extends into said forming chamber from a midsection of said at least one of said upstream and downstream endwalls.

4. The ALFS of claim 1 wherein said first distributing means includes first and second cylindrical distributing screens each for supplying said first material.

5. The ALFS of claim 4 wherein said baffle member extends to a centerline of at least one of said first and second cylindrical distributing screens.

6. The ALFS of claim 4 wherein said baffle member is supported between said first and second cylindrical distributing screens and includes at least one exit path.

7. The ALFS of claim 1 wherein said baffle member includes upper and lower planar sections defining an angle therebetween, wherein said upper planar section is attached to said at least one of said upstream and downstream endwalls.

8. The ALFS of claim 7 wherein said lower planar section extends into said forming chamber.

9. The ALFS of claim 1 wherein said baffle member includes an arcuate section including an upper portion connected to said at least one of said upstream and downstream endwalls and a lower portion extending into said forming chamber.

10. The ALFS of claim 1 further comprising;
cover means for covering said baffle member to reduce intermixing of said first and second materials in said forming chamber before said second material exits said baffle member.

11. The ALFS of claim 10 wherein said cover means includes upper and lower planar sections forming an angle therebetween, said lower planar section being connected adjacent and parallel said upper planar portion of said baffle member, and said upper and lower planar sections defining a gap therebetween for passage of said second material between said baffle member and said cover means.

12. In an air laying forming station (ALFS) for forming an nonwoven substrate from a first material and a second material having at least one physical characteristic substantially different from said first material, said ALFS including a forming chamber, forming means for receiving deposit of said first and second materials, first distributing means for supplying said first material, and flow means for providing an air flow which deposits said first material onto said forming means, an improvement comprising:
second distributing means for delivering said material, independently from said first material between delivery of said first material and said forming means, by gravity along a baffle member.

13. The improved ALFS of claim 12 wherein said baffle member is connected to at least one of said upstream and downstream endwalls and extends into said forming chamber.

14. A method of forming a substrate in an air laying forming station from first and second materials, wherein at least one physical characteristic of said second material is substantially different from said first material, and wherein said ALFS includes a forming chamber, forming means, moving relative to said forming chamber, for receiving deposit of said first and second materials, first distributing means for supplying said first material, and flow means for providing an air flow which deposits said first material onto said forming means, comprising the steps of: feeding said second material, independently from said first material between delivery of said first material and said forming means, by gravity along a baffle member.

15. The method of claim 14 further comprising the step of:
feeding said second material onto said baffle member connected to at least one of said upstream and downstream endwalls.

16. The method of claim 15 further comprising the step of:
extending said baffle member into said forming chamber from a midsection of said at least one of said upstream and downstream endwalls.

17. The method of claim 14 wherein said first distributing means includes first and second cylindrical distributing screens each for supplying fiber, and wherein said baffle member extends to a centerline of at least one of said first and second cylindrical distributing screens.

18. The method of claim 15 wherein said baffle member includes upper and lower planar sections defining an angle therebetween, and further comprising the step of:
attaching said upper planar section to said at least one of said upstream and downstream endwalls so that said lower planar section extends into said forming chamber.

19. The method of claim 15 wherein said baffle member includes an arcuate section including an upper portion connected to said at least one of said upstream and downstream endwalls and a lower portion extending into said forming chamber.

20. The method of claim 15 further comprising:
reducing intermixing of said first and second materials in said forming chamber before said second material exits said baffle member using a cover, wherein said cover includes upper and lower planar sections forming an angle therebetween, said lower planar section being connected adjacent and parallel said upper planar portion of said baffle member, and said upper and lower planar sections defining a gap therebetween for passage of said second material between said baffle member and said cover means.

* * * * *